United States Patent [19]

Ison

[11] Patent Number: Plant 7,267

[45] Date of Patent: Jul. 10, 1990

[54] SUPREME

[76] Inventor: William G. Ison, Rte. 1, Box 19, Hwy. 19, Brooks, Ga. 30205

[21] Appl. No.: 167,324

[22] Filed: Mar. 11, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Black Fry and the pollen parent variety Dixieland to produce an improved variety of muscadine grape.

1 Drawing Sheet

DESCRIPTION OF THE VARIETY

Supreme is a cross between the female variety Black Fry and the pollen parent variety Dixieland.

The primary objective of the breeding was to produce an improved variety of muscadine grape; the fruit of which would be large and black. Additional characteristics include even ripening, high sugar content, dry scar for longer shelf life, high quality; and the plant to be productive and vigorous.

In comparison with both the seed and pollen parent, the new variety is similar in size to the seed parent and also resembles in color the seed parent. The fruit of this new variety contains an average of 24% soluble solids, which sugar content is higher than the pollen parent or the seed parent. The new variety is similar to the seed parent in that it has a dry scar. The present variety yields on the average of 6 to 8 tons per acre in tests conducted at Ison's Nursery & Vineyards, Brooks, Ga.

Asexual reproduction of the new variety either by soft-wood cuttings or by layering as performed at Brooks, Ga., shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type vine: Vine.
Seed parent: Black Fry.
Pollen Parent: Dixieland.

Propagation: Holds its characteristics through succeeding propagation by either layering of by soft-wood cuttings.
Locality where grown: Brooks, Ga.
Fruit borne: In clusters of approximately 5 to 12 berries per cluster.
Fruit size: Large, similar in size to the seed parent and the pollen parent: diameter 1¼".
Fruit color: Greyed Purple Group 187A Fan 4 of The Royal Horticultural Society, London, England.
Sugar content: Average 24% soluble solids.
Fruit Shape: Round.
Seed: Average diameter ⅛ inch, average seed per berry 2.5.
Pulp: A. Color Group Greyed Green, 187A Fan 4 Royal Horticultural Society, London, England. B. Consistency, medium soft, medium juicy as compared to most muscadine varieties.
Skin: Semi-thick, edible.
Foliage: Leaf color, Green Group, 139 C Fan 3 Royal Horticulture Society, London, England. Leaf size and shape similar to most muscadine varieties.
Reproductive organs:
*Pistillte.*—Not self-pollinating. Note: this is a female variety which can be reproduced from cuttings but when planted will not pollinate other varieties.
Growth habits: Vine vigorous and productive; requires support.
Canes: Medium.
Maturity date: Usually ripens about October 10 at Brooks, Ga.
Diseases: Slight susceptibility to Black Rot.

This description was made from a muscadine vine grown at Ison's Nursery & Vineyards, Route 1, Brooks, Ga. 30205.

I claim:

1. The new and distinct variety of grape plant as described and illustrated.

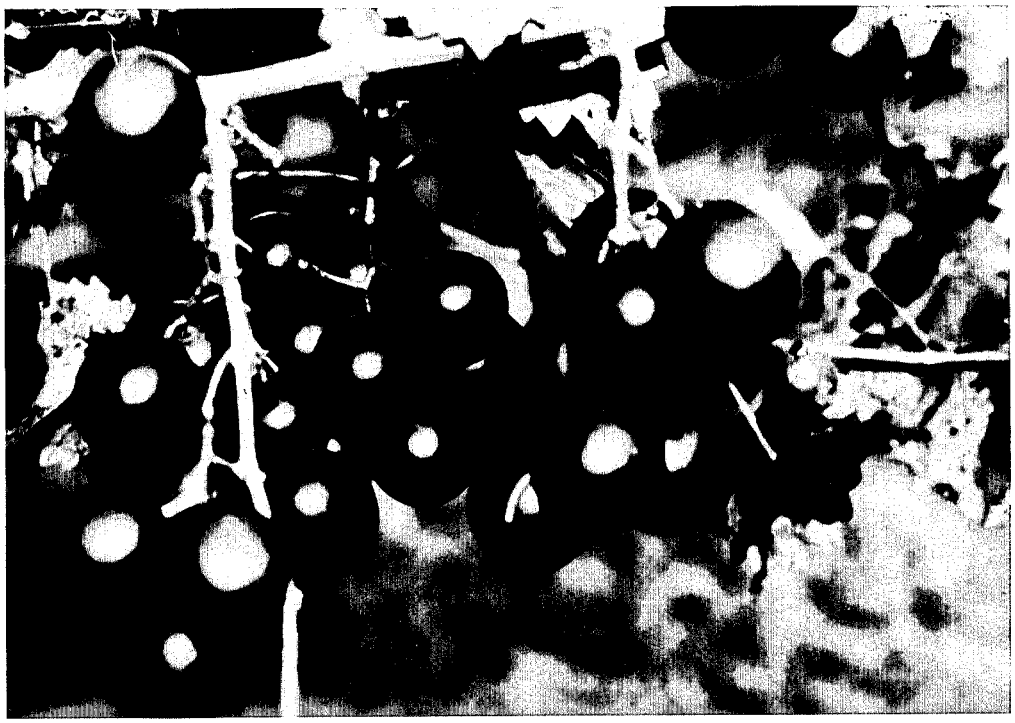

* * * * *